(12) United States Patent
Segler

(10) Patent No.: US 7,097,647 B2
(45) Date of Patent: Aug. 29, 2006

(54) TARSAL JOINT SPACE DISTRACTOR

(76) Inventor: Christopher Paige Segler, 79 Montrose Ave., Daly City, CA (US) 94015

( * ) Notice: Subject to any disclaimer, the term of this patent is extended or adjusted under 35 U.S.C. 154(b) by 543 days.

(21) Appl. No.: 10/248,512

(22) Filed: Jan. 25, 2003

(65) Prior Publication Data
US 2004/0147935 A1 Jul. 29, 2004

(51) Int. Cl.
A61B 17/58 (2006.01)
(52) U.S. Cl. ........................................................ 606/90
(58) Field of Classification Search ................. 600/215, 600/216, 218, 220, 222, 224, 225; 606/86, 606/90
See application file for complete search history.

(56) References Cited

U.S. PATENT DOCUMENTS

| 390,561 | A | 10/1888 | Brown |
|---|---|---|---|
| 569,839 | A | 10/1896 | Roeloffs |
| 2,217,968 | A | 10/1940 | Radcliff |
| 2,757,666 | A | 8/1956 | Grant |
| 3,038,467 | A | 6/1962 | Souatkin |
| 3,470,872 | A | 10/1969 | Grieshaber |
| 3,750,652 | A | 8/1973 | Sherwin |
| 3,916,907 | A | 11/1975 | Peterson |
| 4,034,746 | A | 7/1977 | Williams |
| 4,754,746 | A | 7/1988 | Cox |
| 4,898,161 | A | 2/1990 | Grundei |
| D309,946 | S | 8/1990 | Torre |
| D314,826 | S | 2/1991 | Torre |
| D317,202 | S | 5/1991 | Torre |
| 5,307,790 | A | 5/1994 | Byrne |
| 5,351,680 | A | 10/1994 | Jung |
| D411,299 | S | 6/1999 | Farascioni et al. |
| D411,883 | S | 7/1999 | Farascioni et al. |
| 5,931,777 | A | 8/1999 | Sava |
| 5,944,658 | A | 8/1999 | Koros et al. |
| 5,957,836 | A | 9/1999 | Johnson |
| D417,276 | S | 11/1999 | DeFonzo |
| 5,976,125 | A | 11/1999 | Graham |
| 6,017,305 | A | 1/2000 | Bonutti |
| 6,096,046 | A | 8/2000 | Weiss |
| 6,214,004 | B1 | 4/2001 | Coker |
| 6,224,545 | B1 | 5/2001 | Cocchia et al. |
| 6,241,659 | B1 | 6/2001 | Bookwalter et al. |
| 6,261,296 | B1 * | 7/2001 | Aebi et al. ................. 606/90 |
| D453,377 | S | 2/2002 | Schollhorn et al. |

* cited by examiner

Primary Examiner—Eduardo C. Robert
Assistant Examiner—Michael J. Araj
(74) Attorney, Agent, or Firm—W. Allen Marcontell

(57) ABSTRACT

This disclosure relates to an improved dual axis surgical retractor for use by orthopedic or podiatric surgeons for controlled distraction of tarsal joints or compression of osseus fragments. This retractor generally consists of a pair of screw actuated retractor arms, the tips of which each have apertures for receiving and facilitating temporary pin fixation of the respective tarsal bones to be retracted or osseus fragments to be compressed.

2 Claims, 4 Drawing Sheets

TARSAL JOINT SPACE DISTRACTOR

BACKGROUND OF INVENTION

1. Field of the Invention

The present invention relates to a device and method for spreading adjacent tarsal bones to facilitate surgical procedures within the joint space. More specifically, the present invention relates to a distractor device shaped and configured to allow unimpeded access to joint spaces and articular surfaces when approached from dorsal, dorsolateral, or dorsomedial surfaces of the foot. Additionally, the device may be utilized for compression of osseus fragments in achieving internal fixation of small bones that have been fractured.

2. Preliminary Discussion

Foot pain and difficulty in walking are frequent complaints and may result form a wide variety of conditions. Traumatic, septic, or osteoarthritic degeneration of a joint may produce a joint that is painful and debilitating. In other circumstances, connective tissue disorders or neurological derangements may lead to abnormalities of gait that make ambulation difficult. In many instances the most effective treatment may be surgery involving the joints of the foot ankle, namely the tarsal joints. Various surgical procedures are available and known to be effective to restore osseus architecture, eliminate motion at a painful joint, and create a more stable and functional lower extremity. In order to do this, the surgeon must be able to access the articular surfaces found within the joint spaces. During such podiatric surgical procedures, the tarsal joint spaces are most often approached dorsally, dorsomedially, or dorsolaterally. The actual articular surfaces are found between the tarsal bones, and are the focus of many of these procedures. These bones must be separated and held in the retracted position while the surgeon performs various aspects of these procedures including but not limited to denuding of articular cartilage, subchondral drilling, feathering of articular surfaces, and resection of osseus fragments. In these circumstances, the surgeon must insert various instruments into tarsal joint spaces and must utilize some device to hold the joint space open. The present invention relates such a device, for spreading apart adjacent tarsal bones to facilitate unobstructed access to the joint spaces and articular surfaces therein in order that the surgeon utilizing the device may be able to perform various surgical procedures within the joint spaces.

3. Description of Related Art

While previous devices have taken a variety of approaches in addressing the retraction of tissues in order to allow unfettered access to an operative site, the previously conceived devices in one way or another, by their designs impaired access to the articular surfaces by means of insertion of blades, arms, rakes or devices into the joint spaces. Other devices that may have attempted to improve on this concept and retract without inserting objects into the joint space retracted, still limited access to the operative site by bridging the space retracted. In either event, there is restriction of access to the joint space and articular surfaces retracted and operated upon in tarsal joint surgery.

In October 1888 Brown, with U.S. Pat. No. 390,561 Brown presented a device for retraction of tissues in dental procedures. This device utilized a pair of movable handles pivoted on a common pivot pin or hinge for reciprocal expansion or contraction when the handles are reciprocally moved. A pair of blades arranged at perpendicular angles to the shafts of the handles were to be inserted into the space being retracted. The configuration of this retractor is such that insertion of the blades at the distal ends of the retractor arms into tarsal joint spaces would be cumbersome and the articular surfaces retracted would be obscured by the blades of the retraction device denying access to the very surfaces commonly operated upon during such procedures.

In October 1896 Roeloffs, with U.S. Pat. No. 569,839 proposed a retractor utilizing a spring leaf design with various interchangeable prongs or leaflets for insertion into the space to be retracted. While this device would be useful in the retraction of tissues in many procedures, the size and configuration of the various attachments necessarily inserted into the space being retracted is such that these distal ends of the retractor into tarsal joint spaces would be cumbersome and the articular surfaces retracted would be obscured by the distal aspects of the retraction device denying access to the very surfaces commonly operated upon during such procedures.

In October 1940 Radcliff, with U.S. Pat. No. 2,217,968 presented a pivoted retractor comprised of variously configured hinged opposed leaves to grasp and retract tissues. While this device would be useful in the retraction of soft tissues, the size and configuration of the teeth of this retractor is such that insertion of the distal ends of the retractor arms into tarsal joint spaces would be cumbersome and the articular surfaces retracted would be obscured by the distal aspects of the retraction device denying access to the very surfaces commonly operated upon during such procedures.

In November 1975 Peterson, with U.S. Pat. No. 3,916,907 presented a surgical retractor for use in spinal surgery having a pair of elongated members pivotally attached intermediate their ends. A primary embodiment of this invention was the partial-circularly shaped plates extending outward from adjacent opposite free ends of the respective members. The size and configuration of the ends of this retractor are such that insertion of the distal ends of the retractor arms into tarsal joint spaces would be cumbersome and the articular surfaces retracted would be obscured by the blades of the retraction device denying access to the very surfaces commonly operated upon during such procedures.

In July 1977 Williams, with U.S. Pat. No. 4,034,746 presented a surgical retractor of the type having a pair of movable handles pivoted on a common pivot pin or hinge for reciprocal expansion or contraction when the handles are reciprocally moved. The size and configuration of this retractor is such that insertion of the distal ends of the retractor arms into tarsal joint spaces would be cumbersome and the articular surfaces retracted would be obscured by the blades of the retraction device denying access to the very surfaces commonly operated upon during such procedures.

In July 1988 Cox, with U.S. Pat. No. 4,754,746 presented a retractor utilizing opposing jaws pivoted together and extend oppositely from handles manually swingable to move the jaws relatively toward and away from each other. Generally rectangular blades extend downward from the swinging ends of the jaws and have planar leading bottom portions contiguously engageable for fitting between closely adjacent bones such as metatarsals. The jaws are swung apart to spread the bones and maintain them in spread-apart condition for convenient access to the facing surfaces of the bones. In the case of tarsal joint surgery, this device would be ineffective because the size and configuration of this retractor is such that insertion into tarsal joint spaces would be cumbersome and the articular surfaces retracted would be obscured by the blades of the retraction device denying access to the very surfaces commonly operated upon during such procedures.

In August 1990 Torre, with U.S. Pat. No. D309,946 presented a scissored hinge type retractor utilizing opposed u-shaped tongs designed to grasp metatarsal shafts and retract metatarsal heads. The curved ends of this device make it unsuitable for insertion into the tarsal joints for retraction.

In February 1990 Grundei, with U.S. Pat. No. 4,898,161 presented a scissor hinged type vertebral retractor utilizing pins as the means of engaging adjacent vertebral bodies to be retracted. With this device, the pins are parallel the distracting mechanism, and because they lie in the same plane, distraction of small tarsal bones with this device would require that some portion of the device bridge the distracted joint space, obscuring the view and partially blocking access to the space retracted.

In February 1991 Torre, with U.S. Pat. No. D314,826 presented a scissorred hinge type short bone retractor utilizing curved barrel sections to grasp and retract shafts of curved bones. The curved ends of this device make it unsuitable for insertion into the tarsal joints for retraction.

In May 1991 Torre, with U.S. Pat. No. D317,202 presented an ornamental design for a surgical bone retractor. The size and configuration of this retractor is such that insertion into tarsal joint spaces would be cumbersome and the articular surfaces retracted would be obscured by the blades of the retraction device denying access to the very surfaces commonly operated upon during such procedures.

In May 1994 Byrne, with U.S. Pat. No. 5,307,790 presented a bracelet retractor assembly designed to encircle an extremity and retract skin and soft tissue of the incisional approach, but would be ineffective in applying the necessary force to retract tarsal joint without applying crushing type forces to surrounding soft tissues.

In October. 1994 Jung, with U.S. Pat. No. 5,351,680 presented a manual surgical retraction device suitable for retraction of soft tissue during procedures such as gall bladder surgery, but ineffective for the retraction of bone and joint spaces.

In June 1999 Farascioni et al., with U.S. Pat. No. D411,299 presented an ornamental design for a surgical retractor. The size and configuration of this retractor is such that insertion into tarsal joint spaces would be cumbersome and the articular surfaces retracted would be obscured by the blades of the retraction device denying access to the very surfaces commonly operated upon during such procedures.

In July 1999 Farascioni et al., with U.S. Pat. No. D411,883 presented an ornamental design for a surgical retractor. The size and configuration of this retractor is such that insertion into tarsal joint spaces would be cumbersome and the articular surfaces retracted would be obscured by the blades of the retraction device denying access to the very surfaces commonly operated upon during such procedures.

In August 1999 Sava, with U.S. Pat. No. 5,931,777 presented a tissue retractor comprising a pair of pivotally linked arms, each with a blade mounted thereto by a ball and socket joint to allow the blades free movement relative to the arms. The size and configuration of this retractor is such that insertion into tarsal joint spaces would be cumbersome and the articular surfaces retracted would be obscured by the blades of the retraction device denying access to the very surfaces commonly operated upon during such procedures.

In August 1999 Koros et al., with U.S. Pat. No. 5,944,658 presented a lumbar laminectomy retractor and distractor system comprised of one or more retractor frames including retractor blades for placement in an incision. The blades can be placed in an incision and then engaged by a retractor frame to spread the incision for viewing the surgical site. The size and configuration of this retractor is such that insertion into tarsal joint spaces would be cumbersome and the articular surfaces retracted would be obscured by the blades of the retraction device denying access to the very surfaces commonly operated upon during such procedures.

In September 1999 Johnson, with U.S. Pat. No. 5,957,836 presented a rotatable retractor instrument for expanding a body joint is disclosed. A flattened portion is provided at the distal end of the instrument. With the flattened portion inserted within the joint, rotation of a handle at the instrument's proximal end spreads the joint. The size and configuration of this retractor is such that insertion into tarsal joint spaces would be cumbersome and the articular surfaces retracted would be obscured by the blades of the retraction device denying access to the very surfaces commonly operated upon during such procedures.

In November 1999 Graham, with U.S. Pat. No. 5,976,125 presented an external fixation apparatus for reduction and distraction of a joint injury such as fracture or dislocation of the proximal and distal bones of a joint from a location external to the soft tissue of a patient. This device included a proximal fixator, a distal fixator, a proximal wire inserted through the proximal fixator and into a proximal bone, a distal wire inserted through the distal fixator and into a distal bone, and an adjustable distraction mechanism connecting said proximal and distal fixators. This device is designed primarily for external fixation rather than internal distraction during surgery. Additionally, the distractor mechanism is somewhat cumbersome in its method of distraction further improved upon by the present invention with the incorporation of a dual axis screw actuated retractor arms facilitating distraction or compression.

In November 1999 DeFonzo, with U.S. Pat. No. D417,276 presented an ornamental design for a surgical retractor. The size and configuration of this retractor is such that insertion into tarsal joint spaces would be cumbersome and the articular surfaces retracted would be obscured by the blades of the retraction device denying access to the very surfaces commonly operated upon during such procedures.

In January 2000 Bonutti, with U.S. Pat. No. 6,017,305 presented a fluid operated retractor, which may be used to spread a joint such as a knee joint, or a shoulder joint, or may be used to separate tissue planes generally, to improve visualization and create a working space for the surgeon. This retractor is useful in percutaneous fiber optic surgery, but by the nature of introduction of fluid to facilitate the creation of a working space, would be ineffective in open surgical procedure such as tarsal joint surgery.

In April 2001 Coker, with U.S. Pat. No. 6,214,004 presented a vertebral triplanar alignment facilitator to enable a surgeon to make minute vertebrae adjustments during spinal surgery. While well suited to spinal surgery, the size and configuration of this retractor is such that insertion into tarsal joint spaces would be cumbersome and the articular surfaces retracted would be obscured by the blades of the retraction device denying access to the very surfaces commonly operated upon during such procedures.

In May 2001 Cocchia, et al., with U.S. Pat. No. 6,224,545 presented a surgical retractor apparatus comprising a U-shaped thread assembly slidably engaged with a U-shaped rack. The size and configuration of this retractor is such that insertion into tarsal joint spaces would be cumbersome and the articular surfaces retracted would be obscured by the blades of the retraction device denying access to the very surfaces commonly operated upon during such procedures.

In June 2001 Bookwalter, et al., with U.S. Pat. No. 6,241,659 presented a surgical retractor assembly with controlled rotation comprising a blade mounted on a shaft having a controlled degree of rotation and swings down to grip and retract tissue from bone or a hard tissue structure. The size and configuration of this retractor is such that insertion into tarsal joint spaces would be cumbersome and the articular surfaces retracted would be obscured by the blades of the retraction device denying access to the very surfaces commonly operated upon during such procedures.

In February 2002 Scholihornal., with U.S. Pat. No. D453,377 presented an ornamental design for a retractor which would be ineffective as a retractor for tarsal joint surgery because the size and configuration is such that insertion into tarsal joint spaces would be cumbersome and the articular surfaces retracted would be obscured by the retraction devices denying access to the very surfaces commonly operated upon during such procedures.

There is a need, therefore, for a surgical retractor device that is effective in its ability to retract adjacent small osseus structures, such as tarsal bones, without inserting objects into the joint space, without blocking or covering the articular surfaces of the joint being operated upon, and without bridging or otherwise blocking access to the retracted space from a dorsal approach, in order to provide free and unfettered access for the surgeon to the articular surfaces of bones located within such a joint space when those surfaces are to be operated upon.

The present invention employs pre-existing technology with new application that overcomes the limitations of previously conceived inventions within the prior art.

A significant improvement of the present invention over existing devices is the application of a method of small joint space retraction in which adjacent bones are retracted without inserting objects into the joint space, without blocking or covering the articular surfaces of the joint being operated upon, and without bridging or otherwise blocking access to the retracted space from a dorsal approach.

The simplicity of this design contributes to the commercial viability of the product and is a substantial improvement over previous designs and as such, should decrease the operative time of various tarsal joint surgical procedures, thereby decreasing the time a patient undergoes anesthesia and hemostasis of the extremity, and should thereby decrease associated complications of such surgical procedures.

SUMMARY OF INVENTION

The present invention employs many of the advantages of previously conceived methods of joint distraction and tissue retraction without the disadvantages of unnecessary trauma to cortical bone and without impeded access to the operative site within the joint space being distracted. As a result, the present invention is a substantial improvement upon earlier devices, is easily utilized, and is effective in its ability to distract joints of the foot providing access to the articular surfaces for a variety of podiatric surgical procedures utilized in the treatment of foot pain.

BRIEF DESCRIPTION OF DRAWINGS

The invention will be better understood and the objects other than those set forth above will become better apparent when consideration is given to the following detailed description thereof. Such description makes reference to the annexed drawings wherein.

The same reference numerals refer to the same parts through the various Figures.

DETAILED DESCRIPTION

Figure 1:
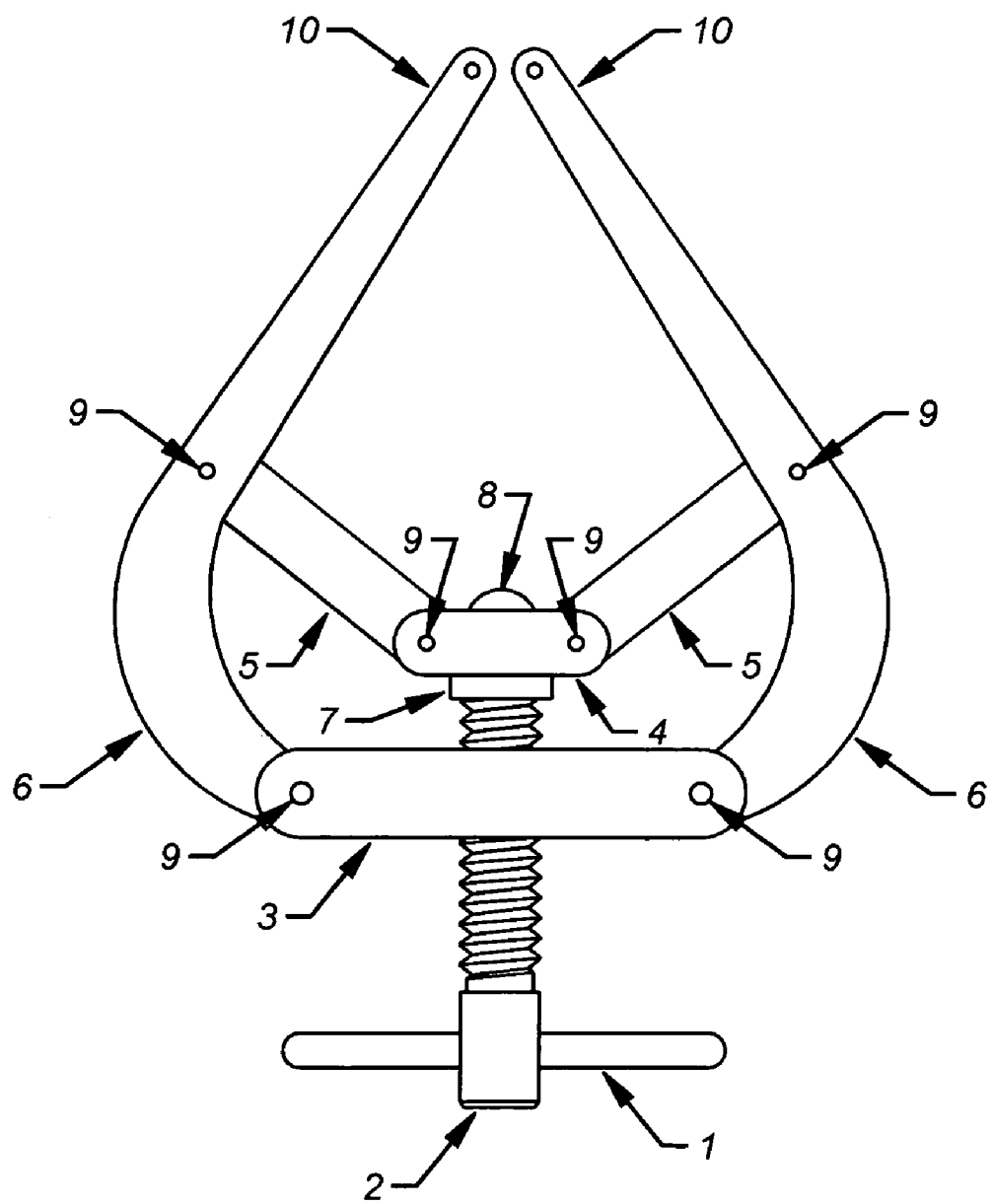
FIG. 1 is a perspective view of the invention as viewed from superiorly or inferiorly, both images being mirror images of the other.
Figure 2:
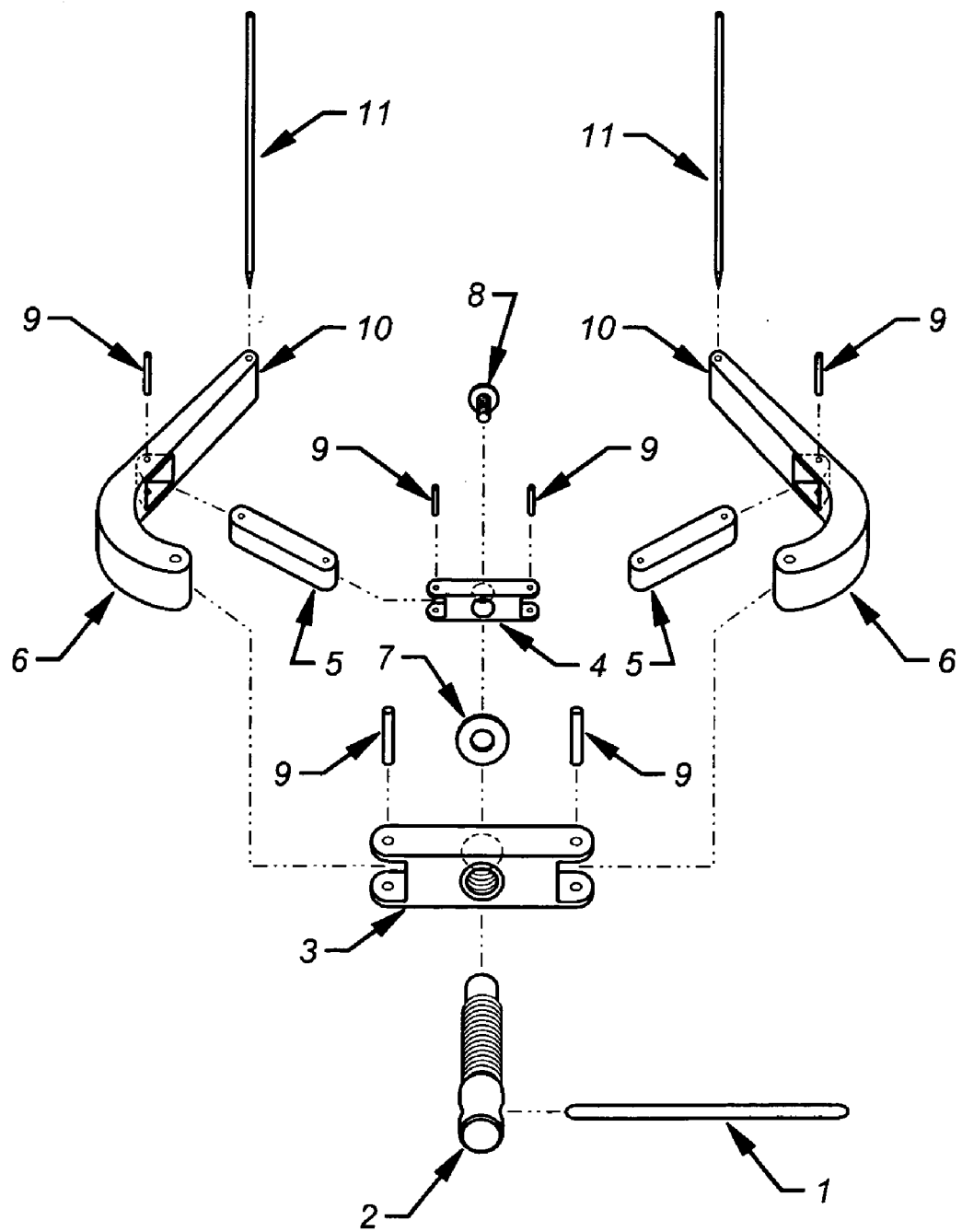
FIG. 2 is an exploded view of the invention as viewed from superiorly and proximally.
Figure 3A:
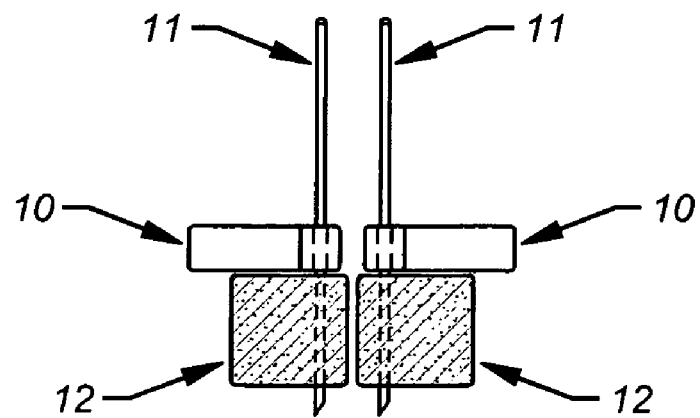
FIG. 3a is an anterior partial perspective view of the invention demonstrating positioning of the device with respect to two-small, opposed bones prior to retraction of the joint space there between. The distal aspects of the retractor arms (10) are positioned on the dorsal aspect of two opposed small bones (12) with temporary pin fixation (11) in place, having been passed from dorsal to plantar, through the apertures in the distal aspects of the retractor arms and subsequently through the bones (12) to be retracted. In the interests of clarity, all aspects of the device aside from the distal aspects of the retractor arms (10) and temporary pin fixation (11) have been eliminated in this view.
Figure 3B:
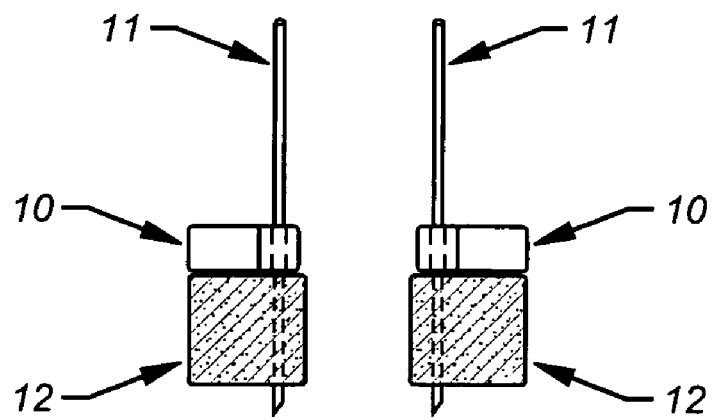
FIG. 3b is an anterior partial perspective view of the invention demonstrating positioning of the device with respect to the retracted two small, opposed bones facilitating retraction of the joint space there between. The distal aspects of the retractor arms (10) are positioned on the dorsal aspect of two opposed small bones (12) with temporary pin fixation (11) in place, having been passed from dorsal to plantar, through the apertures in the distal aspects of the retractor arms and subsequently through the bones (12) with the arms of the device in their retracted position. In the interests of clarity, all aspects of the device aside from the distal aspects of the retractor arms (10) and temporary pin fixation (11) have been eliminated in this view.
Figure 4A:
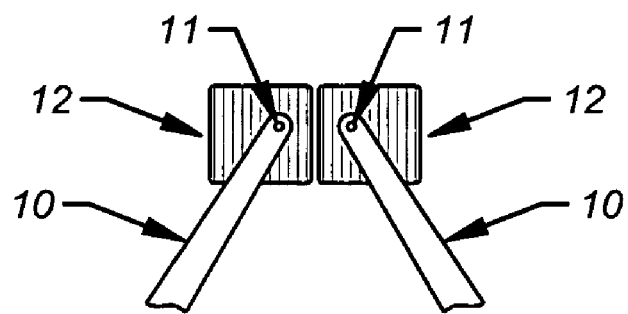
FIG. 4a is a superior partial perspective view of the invention demonstrating positioning of the device with respect to two small, opposed bones prior to retraction of the joint space there between. The distal aspects of the retractor arms (10) are positioned on the dorsal aspect of two opposed small bones (12) with temporary pin fixation (11) in place, having been passed from dorsal to plantar, through the apertures in the distal aspects of the retractor arms and subsequently through the bones (12) to be retracted. In the interests of clarity, all aspects of the device aside from the distal aspects of the retractor arms (10) and temporary pin fixation (11) have been eliminated in this view.
Figure 4B:
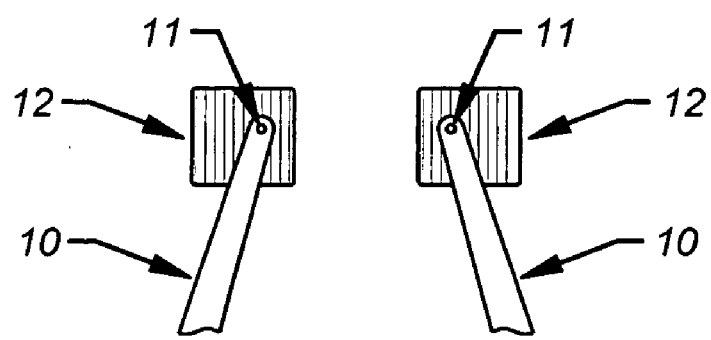
FIG. 4b is a superior partial perspective view of the invention demonstrating positioning of the device with respect to the retracted two small, opposed bones facilitating retraction of the joint space there between. The distal aspects of the retractor arms (10) are positioned on the dorsal aspect of two opposed small bones (12) with temporary pin fixation (11) in place, having been passed from dorsal to plantar, through the apertures in the distal aspects of the retractor arms and subsequently through the bones (12) with the arms of the device in their retracted position. In the interests of clarity, all aspects of the device aside from the distal aspects of the retractor arms (10) and temporary pin fixation (11) have been eliminated in this view.

An improved dual axis joint distractor utilizing temporary pin fixation (11) as a means to facilitate intra-articular surgery by providing retraction without impeding access to the joint surfaces or approach to the joint. Two active extremities (10) are moveably hinged proximally (6) each with a separate hinge allowing movement toward or away from each other. Respective movement of the arms (10) is achieved by a link mechanism that translates rotation of a threaded shaft to arcuate separation movement of the arms.

Clockwise rotation of the levering handle (1) that is centered in the centrally threaded adjusting member (2) results in the distal progression of the distal end of the centrally threaded adjusting member (2) as it passes and rotates through the threaded hole of the primary crossmember (3). The distal end of the centrally threaded adjusting member (2) is suitably fastened to a secondary crossmember (4) by means of a threaded screw (8) passing from distal to proximal through the secondary crossmember (4) through the washer (7), and into a threaded hole in the end of the centrally threaded adjusting member (2). Bilateral lever arms (5) are attached to the secondary crossmember (4) medially and are attached to the mid-portion of the elongated retractor arms (6) laterally. These attachments are facilitated by axels (9) such that rotation about the axis of an axel attaching the various components is permitted. The lateral aspects of the primary crossmember (3) receive the proximal ends of the elongated retractor arms (6) and are also attached with such axels (9) as previously described.

As clockwise rotation of the levering handle (1) and centrally threaded adjusting member (2) commences, distal displacement of the secondary crossmember (4) away from the primary crossmember (3) results in the increase of the angle formed by the bilateral lever arms (5) and the secondary crossmember (4). With this increase in angle, the distance between the points of attachment of the bilateral lever arms (5) and the mid-portions of the elongated retractor arms (6) correspondingly increases as the proximal portion of the elongated retractor arms (6) rotates about their respective axels (9) and facilitates movement of the distal aspects of the elongated retractor arms (10) through which temporary pin fixation (11) has secured said retractor arms to bones (12) or osseus fragments (12) to be manipulated.

The distal aspects of the extremities are suitably arranged with apertures extending through said arms with an axial orientation perpendicular to the plane of movement of said arms (10). Following a surgical opening of soft tissue covering the objective joint, pins (11) are driven through these apertures and concomitantly through the cortical and cancellous bone of the osseus members (12) to be retracted. As previously described, clockwise rotation of the centrally threaded adjusting member (2) translates into lateral movement of the hinged active extremities (10) with pins (11) affixing said members to the bones (12) adjacent the joint space, thereby forcibly and precisely retracting the bones (12) and distracting the joint space.

Conversely, counter-clockwise rotation of the centrally threaded adjusting member (2) translates into medial movement of the hinged active extremities (10) with pins (11) affixing said members to the bones (12) adjacent the joint space or adjacent osseus fragments (12), thereby forcibly and precisely compressing said bones or fragments.

Once the desired surgical results have been obtained and retraction and or compression of the corresponding bones or osseus fragments is no longer required, the device and pins facilitating temporary fixation may be removed, and the surgical site then closed.

Objects of the Invention

It is an object of the present invention, therefore, to provide a device and method for spreading joints of the foot and holding that joint space open.

It is a further object of the present invention that to provide a device and method for providing compression of osseus fragments as needed in utilization of internal fixation of small bone fractures.

It is a still further object of the present invention that the device be fully adjustable with respect to the amount of joint space distraction or force of compression.

It is a still further object of the present invention that the device may be applied to and thus distract a number of different small and large joints of the foot.

It is a still further object of the present invention that the device may be applied to and thus compress a variety of different small and large osseus fragments or fractured bones.

It is a still further object of the present invention that the device be self-retaining with respect to the joint distracted.

It is a still further object of the present invention that the device be configured in such a manner that the jaws facilitating distraction be positioned at perpendicular angles to the articular surfaces of the joint being distracted.

It is a still further object of the present invention that the device be configured in such a manner as to permit denuding, feathering, and subchondral drilling of the articular surfaces of the joint being distracted.

It is a still further object of the present invention that the device be configured in such a manner as to permit insertion of a bone graft or bone grafting materials into the joint space being distracted.

It is a still further object of the present invention to provide a joint distraction without the device blocking dorsal access to the joint space.

It is a still further object of the present invention to provide joint distraction without the device blocking the articular surfaces within the joint space.

It is a still further object of the present invention that the device distracts the joint atraumatically with respect to the dorsal cortical bone immediately adjacent to the joint surfaces being distracted.

Description of the Preferred Embodiment

The first embodiment of a surgical retractor in accordance with the invention is formed by the novel combination of a pair of screw actuated retractor arms (6 & 10) and temporary pin fixation (11) as a means to facilitate small bone (12) retraction and expose the joint spaces therein.

It is a further embodiment of the invention that the centrally threaded adjusting member (2) be located at a site remote form the joint space being retracted so that no portion of the device be necessarily situated in a location that would obstruct access to the joint space being retracted.

It is a further embodiment of the invention that the joint space retractor be capable of withstanding exposure to the conditions encountered in the various processes of autoclave or chemical sterilization without sustaining damage to the substance of the joint space retractor.

The invention claimed is:

1. A joint space distractor comprising:
   a pair of retractor arms, each arm having a distal end and a pivot end:
   a first crossmember having a pair of first pivot joint connections respective to the pivot ends of said retractor arms to accommodate arcuate movement of said retractor arms in a substantially common arc plane;
   an adjustment member having a threaded attachment to said first crossmember between said first pivot joint connections for displacement along an adjustment axis respective to attachment member threads, said adjustment member having a first distal end on one side of said first crossmember and a second distal end on an opposite side of said first crossmember;

a second crossmember secured to said first distal end of said adjustment member at a fixed position along said adjustment axis for rotation about said axis;

a pair of links, each link having a pivot connection to said second crossmember and to a respective retractor arm at a second pivot joint disposed between said first pivot joint and said retractor arm distal end;

guide apertures through respective distal ends of said retractor arms, said guide apertures each having a guide axis disposed transversely of said common arc plane; and, bone pins confined within said guide apertures for translation along respective guide axes, said bone pins each having a bone piercing end for penetration respectively contiguous elements of a bone joint.

2. A method of accessing contiguous articular surfaces respective to adjacent bones of an articulating joint comprising the steps of:

providing a pair of retractor arms, each arm having a distal end and a pivot end;

providing a crossmember for pivotally securing said retractor arm pivot ends for arcuate arm movement confined substantially within a common plane;

providing a threaded linkage mechanism for arcuately displacing the distal ends of said retractor arms within said common plane;

providing guide apertures through respective distal ends of said retractor arms, said guide apertures each having a guide axis disposed substantially normal to said common plane;

confining axially elongated bone piercing pins within each of said guide apertures for axial translation;

surgically opening an articulation joint;

piercing contiguous bones of said joint by said confined piercing pins at respective locations displaced from an articular space between said contiguous bones; and separating said contiguous bones to expose contiguous articular surfaces by arcuately displacing said retractor arm distal ends.

* * * * *